US007123686B2

(12) United States Patent
Sakata

(10) Patent No.: US 7,123,686 B2
(45) Date of Patent: Oct. 17, 2006

(54) APPARATUS AND METHOD FOR X-RAY ANALYSIS

(75) Inventor: Masataka Sakata, Tokyo (JP)

(73) Assignee: Rigaku Corporation, Akishima (JP)

( * ) Notice: Subject to any disclaimer, the term of this patent is extended or adjusted under 35 U.S.C. 154(b) by 106 days.

(21) Appl. No.: 10/772,303

(22) Filed: Feb. 6, 2004

(65) Prior Publication Data
US 2004/0156471 A1    Aug. 12, 2004

(30) Foreign Application Priority Data
Feb. 7, 2003   (JP)   ............... 2003-030431

(51) Int. Cl.
*G01N 23/20* (2006.01)
*G01N 23/207* (2006.01)
(52) U.S. Cl. ......................... 378/71; 378/79
(58) Field of Classification Search ............. 378/71, 378/73, 79, 81, 82, 84
See application file for complete search history.

(56) References Cited
U.S. PATENT DOCUMENTS
5,446,777 A    8/1995   Houtman 6,285,736 B1 *   9/2001   Dosho .................... 378/79

FOREIGN PATENT DOCUMENTS

| GB | 2270230 A | * | 3/1994 |
|----|-----------|---|--------|
| JP | 04161843 A | * | 6/1992 |
| JP | 9-229879 | | 9/1997 |
| JP | 09229879 | | 9/1997 |
| JP | 2000-146871 | | 5/2000 |
| JP | 2000146872 | | 5/2000 |

* cited by examiner

*Primary Examiner*—Edward J. Glick
*Assistant Examiner*—Chih-Cheng Glen Kao
(74) *Attorney, Agent, or Firm*—Buchanan Ingersoll & Rooney PC

(57) ABSTRACT

An apparatus for X-ray analysis includes (1) a focusing optical system including an X-ray source, a specimen table and a two-dimensional X-ray detector, (2) a device for shifting the angle of incidence of X-rays relative to a specimen supported by the specimen table, (3) a device for moving the two-dimensional X-ray detector in parallel with a central axis of rotation of the specimen and (4) a mask arranged in front of the two-dimensional X-ray detector. The mask has a slit arranged on a line intersecting a plane rectangularly intersecting the central axis of rotation of the specimen and containing a central optical axis of incident X-rays. The mask is driven to move in parallel with the axis of rotation of the specimen so that measuring can be conducted.

14 Claims, 3 Drawing Sheets

APPARATUS AND METHOD FOR X-RAY ANALYSIS

BACKGROUND OF THE INVENTION

1. Field of the Invention

The present invention relates to an apparatus and a method for analyzing a specimen by means of X-rays.

2. Description of the Related Art

A known X-ray analysis apparatus is described in Japanese Patent Application Laid-Open Publication No. 2000-146871. The known X-ray analysis apparatus is adapted to irradiate a micro-specimen or a micro-part of a specimen with a parallel X-ray beam and detect X-rays diffracted by the micro-specimen or the like by means of a two-dimensional X-ray detector. With the known X-ray analysis apparatus, it is possible to evaluate the grain size and the preferred orientation of the specimen and identify single crystal, strongly oriented polycrystal and amorphism by directly observing a Debye ring by means of the two-dimensional X-ray detector. Additionally, it is possible for the X-ray analysis apparatus to perform various measuring operations that are not allowed to a zero-dimensional X-ray detector such as SC (scintillation counter) or a one-dimensional X-ray detector such as PSPC (position sensitive proportional counter).

In addition to above-described measurement using a parallel X-ray beam, X-ray measurement using a optical system for the focusing method is also known. The focusing method is achieved by using a light diverging slit for causing a divergent beam to strike a specimen, a light receiving slit arranged on a spot region on the focusing circle (also referred to as the Rowland circle) where X-rays diffracted by the specimen are converged and a zero-dimensional X-ray detector arranged behind the light receiving slit as disclosed, for example, in Japanese Patent Application Laid-Open Publication No. 9-229879. With the focusing method, the specimen is driven to rotate around an axial line that runs through the specimen itself, a so-called θ axial line, in order to measure the angle of diffraction 2θ. This rotation is referred to as θ rotation of the specimen.

An X-ray analysis apparatus realized on the basis of the focusing method has an advantage that it provides an excellent resolution and the intensity of the diffracted X-rays is very strong as compared with the above-described parallel beam method. Because of this advantage, the focusing method is being widely used to observe a relatively large specimen such as a powdery specimen covering an area of about 20 mm×10 mm. As pointed out above, X-ray measurement using a two-dimensional X-ray detector and a parallel X-ray beam and X-ray measurement using an optical system for the focusing method have respective advantages and conventionally they are used selectively depending on the situation. However, there arises a problem that two measurement systems need to be held ready at high cost so long as these two modes of measurement are employed selectively. Additionally, there is also a problem that measuring operations selectively using these two modes of measurement are very cumbersome and inconvenient.

Facing of these problems, the inventor of the present invention came to believe that an X-ray measuring operation based on the parallel beam method and an X-ray measuring operation based on the focusing method can be selectively conducted with ease if an optical system for the focusing method can be used for a two-dimensional X-ray detector. However, such a selective use is extremely difficult because of the reason as pointed out below.

When only an optical system for the focusing method is arranged in front of a two-dimensional X-ray detector and the specimen is simply subjected to the θ rotation for measurement on the basis of the focusing method, the two-dimensional X-ray detector picks up not only diffraction intensity data that needs to be obtained but also unnecessary X-rays and hence it is far from possible to obtain practically feasible data with a low S/N ratio.

SUMMARY OF THE INVENTION

In view of the above-identified problem, it is therefore an object of the present invention to realize an observation, using a two-dimensional X-ray detector on the basis of the focusing method, and also provide a two-dimensional X-ray detector that is adapted to observe a specimen on the basis of both the parallel beam method and the focusing method.

An apparatus for X-ray analysis according to the invention, comprising: (1)a focusing method optical system formed by arranging an X-ray source adapted to generate X-rays, a specimen supporting means for supporting a specimen and a two-dimensional X-ray detecting means for detecting X-rays from the specimen so as to satisfy the requirements of the focusing optical system; (2)a means for shifting the angle of incidence of X-rays relative to the specimen by rotating the specimen or the X-ray source around a central axis of rotation passing through the surface of the specimen; (3)a means for moving the two-dimensional X-ray detecting means in parallel with the central axis of rotation; and a mask arranged at a position in front of the two-dimensional X-ray detecting means as viewed from the specimen and having a slit on a line intersecting a plane rectangularly intersecting the central axis of rotation and containing the central optical axis of incident X-rays.

In the above definition, the expression of "the requirements of the focusing optical system" refers to those that are needs to be met in order to irradiate a divergent X-ray beam from an X-ray source located on a focusing circle onto the specimen located on another spot on the focusing circle and detect X-rays diffracted by the specimen and converged onto still another spot located on the same focusing circle.

With an apparatus for X-ray analysis according to the invention, since a mask having a slit is arranged at a position in front of the X-ray receiving surface of a two-dimensional X-ray detecting means, X-rays can be observed by the two-dimensional X-ray detecting means on the basis of the focusing method. Additionally, X-rays can be observed on the basis of the parallel beam method by removing the mask from the front of the two-dimensional X-ray detecting means and replacing the focusing optical system with a parallel beam optical system. In other words, the focusing method and the parallel beam method can selectively be used with ease by using a two-dimensional X-ray detecting means as common X-ray detecting means.

The two-dimensional X-ray detecting means may be a detector plate realized by uniformly forming storage phosphor on the X-ray detecting surface or a CCD X-ray detector realized by arranging CCDs (charge coupled devices) two-dimensionally on the X-ray detecting surface to form a matrix thereof.

The storage phosphor as used herein refers to a material that can accumulate energy at the position where it is irradiated with X-rays so that the accumulated energy can be discharged to the outside as light when it is hit by a stimulating excited beam, a laser beam for instance, at the position.

An apparatus for X-ray analysis having the above described configuration preferably further comprises an X-ray beam switching means adapted to switch the X-ray beam striking the specimen from a divergent beam to a parallel beam or vice versa. Such an X-ray beam switching means may be formed typically by means of a table to which a diverging slit or a collimator can be selectively fitted. The table is arranged at a predetermined position of the X-ray optical system and a diverging slit or a collimator, whichever necessary, is selectively fitted to the table so as to produce an X-ray beam of the required type for use.

An apparatus for X-ray analysis having the above described configuration preferably further comprises a mask supporting means arranged so as to allow the mask to move between a first position located in front of the two-dimensional X-ray detecting means and a second position not located in front of the two-dimensional X-ray detecting means as viewed from the specimen.

With this arrangement, either the focusing method that involves the use of a mask or the parallel beam method that does not involve the use of a mask can be selectively employed with ease. The mask supporting means may be a frame member adapted to removably support a mask or an arm member adapted to move in parallel with the central axis of rotation and slew in a condition where it supports the mask.

In an apparatus for X-ray analysis having the above described configuration, the shift of the angle of incidence of X-rays relative to the specimen and the parallel movement of the two-dimensional X-ray detecting means are preferably synchronized with each other. The expression of "synchronized" as used herein refers to a condition where the two-dimensional X-ray detecting means is moved as a function of the shift of the angle of incidence of X-rays relative to the specimen.

In an apparatus for X-ray analysis having the above-described configuration, the X-ray receiving surface of the two-dimensional X-ray detecting means is preferably that of a cylinder formed around the central axis of rotation of the specimen or the X-ray source so as to shift the angle of incidence of X-rays striking the specimen. With this arrangement, the correspondence of the position for detecting the light receiving surface of the two-dimensional X-ray detecting means and the angle of diffraction $2\theta$ is simplified to facilitate the process of reading the latent image of energy accumulated in the two-dimensional X-ray detecting means.

In another aspect of the present invention, there is provided a method for X-ray analysis using a two-dimensional X-ray detecting means comprising:
   (a) causing X-rays emitted from an X-ray source to strike a specimen in the form of either a divergent beam or a parallel beam; wherein
   (b) in the case of using a divergent beam, the method further comprising steps of:
      (1) shifting the angle of incidence of X-rays striking the specimen by rotating either the specimen or the X-ray source around a central axis of rotation running through the surface of the specimen;
      (2) arranging a mask having a slit in front of the two-dimensional X-ray detecting means so as to make the slit to be located on a line intersecting a plane rectangularly intersecting the central axis of rotation and containing the central optical axis of incident X-rays; and
      (3) moving the two-dimensional X-ray detecting means in parallel with the central axis of rotation in synchronism with the shift of the angle of incidence of X-rays relative to the specimen.

With a method for X-ray analysis according to the invention, X-rays can be observed by a two-dimensional X-ray detecting means on the basis of the focusing method because a mask having a slit is arranged in front of the X-ray receiving surface of the two-dimensional X-ray detecting means. Additionally, it is possible to observe X-rays on the basis of the parallel beam method by removing the mask from the front of the two-dimensional X-ray detecting means and replacing the focusing optical system with a parallel beam optical system. In other words, the focusing method and the parallel beam method can selectively be used with ease by using a two-dimensional X-ray detecting means as common X-ray detecting means.

DETAILED DESCRIPTION OF THE PREFERRED EMBODIMENTS

Figure 1:
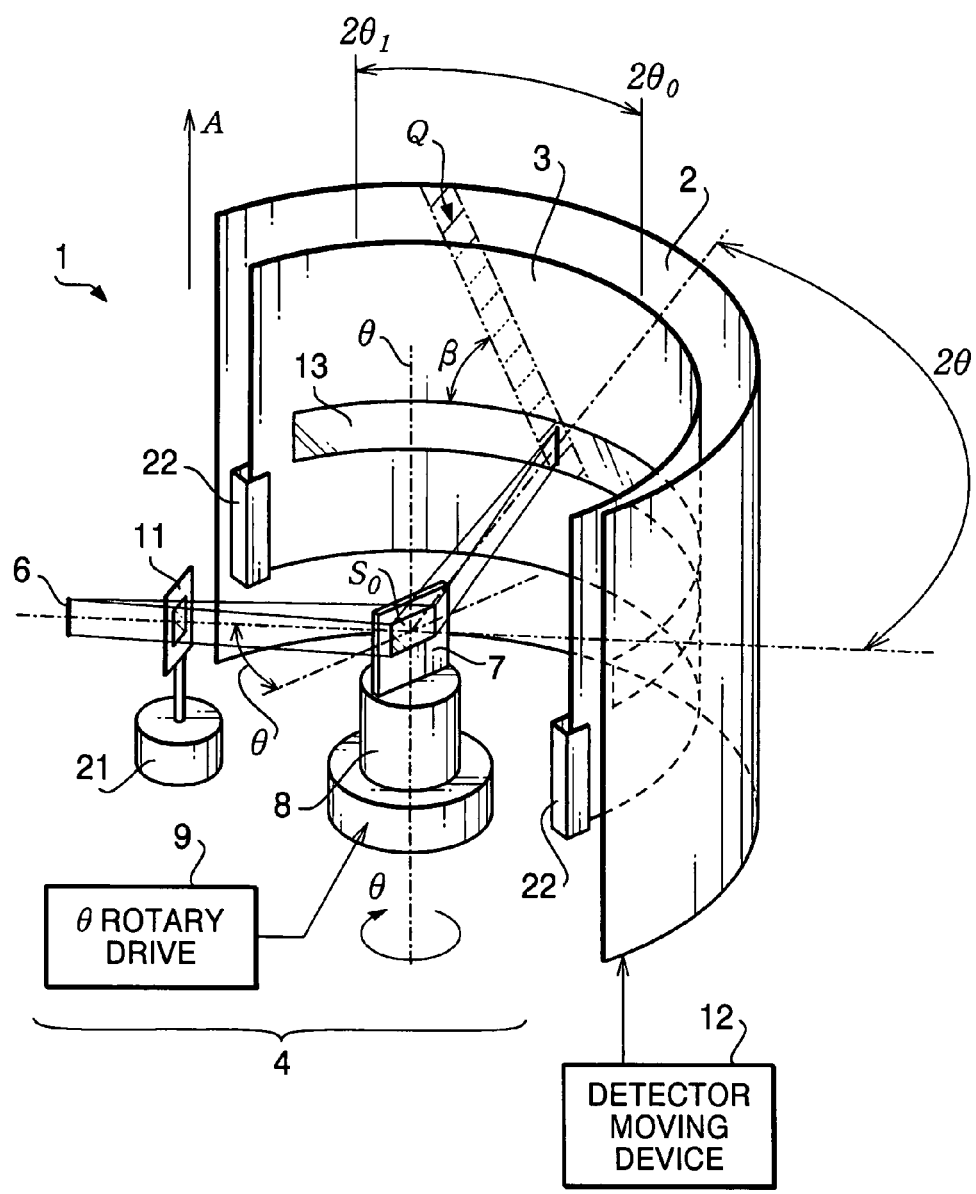
FIG. 1 is a schematic perspective view of an embodiment of apparatus for X-ray analysis according to the present invention when used with a focusing optical system.

Now, the present invention will be described in greater detail by referring to the accompanying drawings that illustrates an embodiment of apparatus and method for X-ray analysis. FIG. 1 is a schematic illustration of the embodiment of an apparatus for X-ray analysis. The apparatus 1 for X-ray analysis comprises a detector plate 2 that operates as two-dimensional X-ray detecting means, a mask 3 arranged in front of the X-ray receiving surface of the detector plate 2, a focusing optical system 4 arranged in front of the mask 3 and a detector moving device 12 for moving the detector plate 2 vertically up and down in FIG. 1 in parallel with the central axis of the apparatus.

The mask 3 has a slit 13 so that X-rays pass only through the slit 13 but otherwise are blocked by the mask 3 so that they cannot pass through the mask 3 in any other areas. The mask 3 is removably supported by support frames 22, which is a mask supporting means. All the X-ray receiving surface of the detector plate 2 can be exposed to X-rays by removing the mask 3 from the support frame 22. Storage phosphor is laid on the entire surface of the X-ray receiving surface of the detector plate 2 to a uniform thickness.

Figure 2:
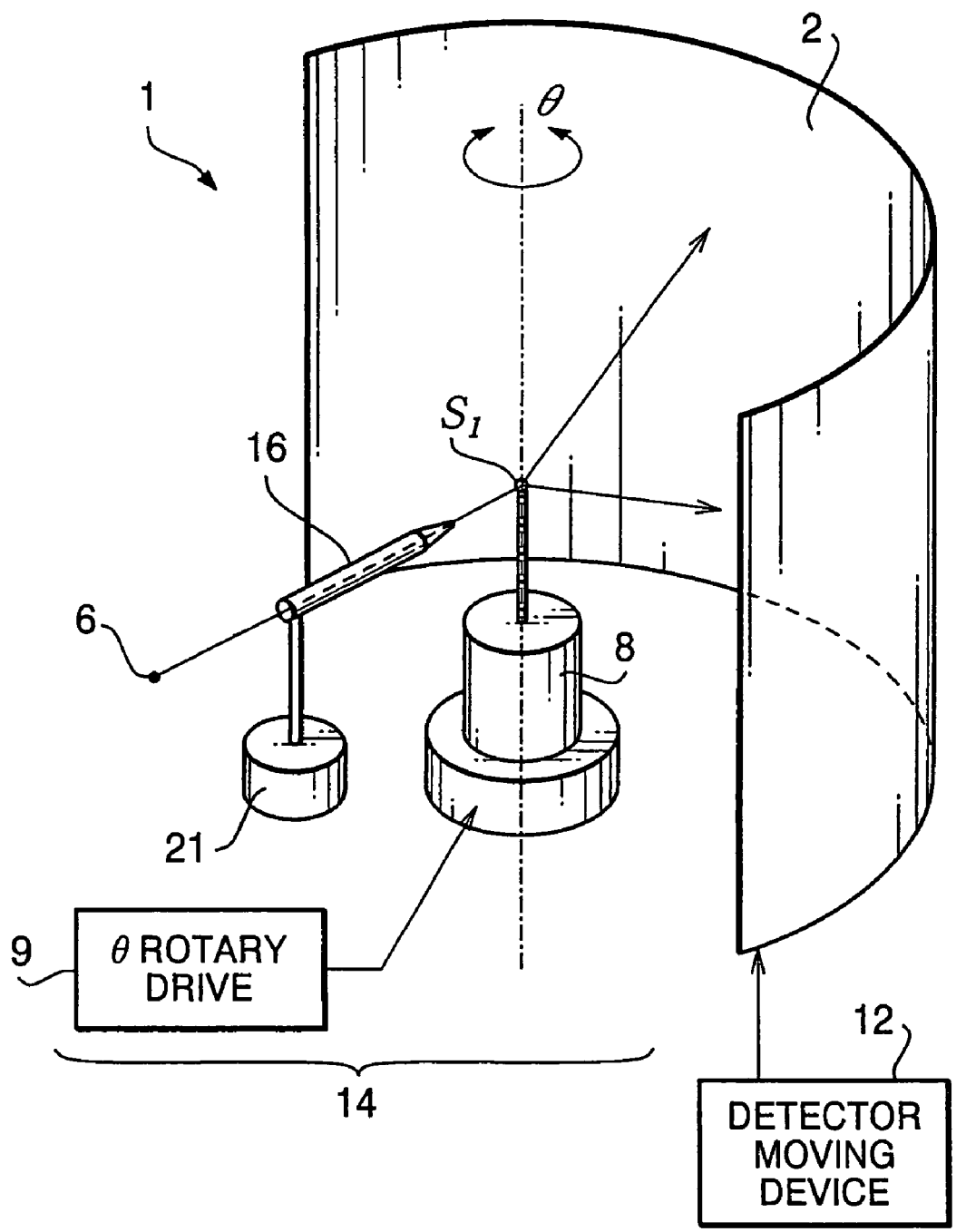
FIG. 2 is a schematic perspective view of the embodiment of apparatus for X-ray analysis according to the present invention when used with a parallel beam optical system.

The focusing optical system 4 includes an X-ray source 6 adapted to generate X-rays, a specimen holder 7 containing a powdery specimen S0, a specimen table 8 to which the specimen holder 7 is fitted, an $\theta$ rotary drive 9 for rotating the specimen table 8 around $\theta$ axial line and a diverging slit 11 for leading divergent X-rays emitted from the X-ray source 6 to the specimen S0. The diverging slit 11 is supported by a table 21 that operates as X-ray beam switching means. The diverging slit 11 can be removed from the table 21 and subsequently another optical system, a collimator 16 for instance, can be mounted as shown in FIG. 2.

To shift the angle of incidence θ of X-rays striking the specimen S0, the specimen S0 is rotated around the θ axial line by an appropriate angle by means of the θ rotary drive 9. Note that the plane that passes through the center of the divergent X-ray beam emitted from the X-ray source 6 and striking the specimen S0 and rectangularly intersects the θ axial line is referred to as X-ray incidence plane hereinafter.

The mask 3 is arranged in parallel with the light receiving surface of the detector plate 2 and the slit 13 has a width (or height) substantially same as the height of the X-ray source 6 and is strip-shaped and coaxial with the light receiving surface of the detector plate 2. The slit 13 is arranged on a line that the mask 3 rectangularly intersects the X-ray incidence plane.

The θ axial line is an axial line extending substantially in parallel with the detector plate 2, which detector plate 2 is adapted to move in a direction "A" that runs in parallel with the θ axial line. The X-ray receiving surface of the detector plate 2 is part of a cylindrical surface formed around the θ axial line.

The X-ray source 6 typically comprises a filament (not shown) that is electrically energized and heated to emit thermoelectrons and a target (not shown) arranged oppositely relative to the filament. The region of the surface of the target that thermoelectrons emitted from the filament collide with is the X-ray focus and X-rays having a wavelength that corresponds to the material of the target are generated from the X-ray focus.

The X-ray focus is generally formed to show a rectangular profile on the target so that an X-ray beam having an oblong cross section, or a so-called line-focused X-ray beam, is produced when X-rays are taken out from the longitudinal direction of the rectangular profile whereas an X-ray beam having a practically squire or circular cross section, or a so-called point-focused X-ray beam, is produced when X-rays are taken out from one of the short sides of the rectangular profile. Thus, a point-focused X-ray beam and a line-focused X-ray beam can be selectively produced by shifting the direction of the X-ray generator including the X-ray source 6. In FIG. 1, the X-ray source 6 is so arranged that a line-focused X-ray beam is produced from the X-ray source 6.

The powdery specimen S0 is so formed that it typically covers an area of 10 mm long and 20 mm wide. The θ rotary drive 9 can be formed, for instance, by using a motor whose angle of rotation can be controlled highly precisely and a drive mechanism including a power transmission means for transmitting the rotary power of the motor to the specimen table 8. The motor may be a pulse motor or a servo motor. The power transmission means may be formed by combining a worm gear and a worm wheel.

The above-described apparatus 1 for X-ray analysis using a focusing optical system 4 operates typically in a manner as described below. X-rays emitted from the X-ray source 6 and whose scope is limited by the diverging slit 11 are irradiated onto the specimen S0 while the specimen is being rotated around the θ axial line for so-called θ rotation by the θ rotary drive 9 and the detector plate 2 is being moved in parallel with the θ axial line in the direction of the arrow "A" by the detector moving device 12 in synchronism with the θ rotation.

As X-rays strike the specimen S0, they are diffracted by the specimen S0 if the Bragg's conditions of diffraction are met between the X-rays and the crystal lattice plane in the specimen S0. When the angle of incidence of X-rays striking the specimen S0 is θ and X-rays are diffracted by the specimen S0, diffracted X-rays are converged to a region on the focusing circle of the angle of diffraction 2θ.

The slit 13 formed in the mask 3 extends rectangularly relative to the θ axial line. Therefore, when X-rays are diffracted by the specimen S0, diffracted X-rays pass through the slit 13 and irradiate the X-ray receiving surface of the detector plate 2 so that a latent image of energy is formed in the storage phosphor of the irradiated area of the X-ray receiving surface. In such a case, X-rays other than diffracted X-rays such as scattered unnecessary rays are blocked by the mask 3 and hence do not get to the detector plate 2. Since the detector plate 2 is driven to move in parallel with the θ axial line in the direction of the arrow "A" in synchronism with the θ rotation, the effective exposure region on the detector plate 2 that is exposed to diffracted X-rays will be the shaded region "Q" in FIG. 1.

Note that the region "Q" is not a point area on the diffracted angle 2θ, but has a predetermined width along the direction of 2θ, namely the direction perpendicular to the θ axial line, namely the direction in which the slit 13 extends. If the width of the region is 2θ±α, the detector plate 2 can pick up data on diffracted X-rays that satisfy the convergence requirements within the region of 2θ±α so that it can catch diffracted X-rays with a sufficient intensity. Therefore, the S/N ratio is improved and the measuring operation can be conducted at high speed. The efficiency of operation is improved when the value of "α" is large, but the resolution of data is reduced when the value of "α" is too large.

Note that θ rotation proceeds continuously or stepwise with a step angle of 1/1,000 to 1/100 degree and the detector plate 2 moves in parallel with the θ axial line in the direction of the arrow "A". The moving speed of the detector plate 2 defines the angle "β" of the locus "Q" to be recorded. It is desirable to select a value that is as large as possible for the angle "β" because the obtained data are more isolated to improve the S/N ratio when the angle "β" is large.

As the measuring operation terminates within the region for measuring the angle of diffraction to be detected between 2θ0 and 2θ1, the detector plate 2 is loaded onto a predetermined position of a reading device (not shown) for a reading process. In the information read by the reading device, the longitudinal direction indicated by arrow "A" in the exposure region "Q" provides information on the same diffracted X-rays and information on the intensity of diffracted X-rays for a single angle of diffraction is obtained by integrating the data in the longitudinal direction.

An X-ray measuring operation using the focusing optical system is performed on the powdery specimen S0 having a relatively large area by means of the above described process. Although it is conventionally very difficult to perform an X-ray measuring operation, using a focusing optical system and a detector plate 2 that is a two-dimensional X-ray detecting means, it is now possible to perform such an operation that involves the use of a focusing optical system by arranging a mask 3 having a slit 13 in front of the detector plate 2, while moving the detector plate 2 in parallel with the θ axial line in the direction of the arrow "A", and integrating the data obtained in a predetermined region "Q" for the longitudinal direction indicated by the arrow "A" as in the case of the above-described embodiment.

Since the two-dimensional X-ray detecting means can pick up information on diffracted X-rays in a region at and near the angle of diffraction 2θ defined by 2θ±α, it is now possible to obtain information on diffracted X-rays with a sufficient level of intensity so that the measuring operation can be conducted at high speed.

An X-ray measuring operation using the parallel beam method can be conducted replacing the above-described focusing optical system with the parallel beam optical system. FIG. 2 shows a typical arrangement of optical system in an apparatus 1 for X-ray analysis according to the invention. An X-ray measuring operation using the parallel beam method is used for a micro-specimen S1 or a micro-part of a specimen.

The arrangement of the apparatus 1 for X-ray analysis shown in FIG. 1 can be changed to the arrangement of FIG. 2 typically in a manner as described below. Firstly, the mask 3 is removed from the support frame 22 (see FIG. 1) to expose the entire X-ray receiving surface of the detector plate 2. Then, the diverging slit 11 is removed from the table 21 and the collimator 16 is mounted onto the table 21 as replacement. Additionally, the specimen holder 7 (see FIG. 1) is removed from the specimen table 8 and the micro-specimen S1 is fitted to the table 8 as replacement. While the detector moving device 12 is connected to the detector plate 2, it is not operated for a measuring operation using the parallel beam method. In other words, the detector plate 2 is held stationarily to a given position.

A parallel beam optical system 14 includes the specimen table 8 that is located at the position same as its position for the focusing optical system 4 as shown in FIG. 1, the X-ray source 6, the collimator 16 that operates as parallel beam forming means and the θ rotary drive 9 for rotating the specimen table 8 to rotate around the θ axial line.

The X-ray source 6 is the one used for the focusing optical system 4 shown in FIG. 1. Note, however, that the X-ray source 6 shown in FIG. 2 is modified in terms of mode of taking out X-rays from the X-ray focal point so that point-focused X-rays can be taken out of it. Divergent X-rays coming from the X-ray source 6 are turned to a parallel X-ray beam having a very small cross section by the collimator 16, which then irradiates the micro-specimen S1.

The apparatus 1 for X-ray analysis using the parallel beam optical system 14 typically operates in a manner as described below. The specimen S1 is turned continuously around the θ axial line for measuring while the detector plate 2 is held stationarily to a given position.

Then, X-rays are generated by the X-ray source 6 and generated X-rays are turned to a parallel beam by the collimator, which then irradiates the micro-specimen S1. At this time, if the Bragg's conditions of diffraction are met between X-rays striking the specimen S1 and the crystal lattice plane in the specimen and diffracted X-rays, X-rays are diffracted by the specimen S1 and diffracted X-rays irradiate the surface of storage phosphor on the detector plate 2 so that a latent image of energy is formed in the irradiated area. In this way, a Debye ring can be two-dimensionally directly observed for the specimen S1 by means of the detector plate 2.

Thus, as described above, according to the invention, an X-ray measuring operation using a focusing optical system as shown in FIG. 1 or an X-ray measuring operation using a parallel beam optical system as shown in FIG. 2 can be selectively performed without difficulty by using a mask 3 as shown in FIG. 1 or not using such a mask 3 and by operating the focusing optical system 4 or the parallel beam optical system 14, whichever appropriate, while the detector plate 2, which is a two-dimensional X-ray detector that operates as X-ray detecting means, is disposed at the same position.

Since the focusing optical system 4 shown in FIG. 1 and the parallel beam optical system 14 shown in FIG. 2 share a considerable number of components, they can be realized at very low cost if compared with an arrangement case where the two optical systems are prepared separately.

Additionally, since a mask 3 having a slit 13 is arranged in front of the detector plate 2 in this embodiment of apparatus 1 for X-ray analysis, the X-ray detector, which is a two-dimensional X-ray detector, can be used for the focusing optical system 4 to enhance the level of component sharing of the apparatus for X-ray analysis.

(Another Embodiment of Apparatus for X-ray Analysis)

Figure 3:
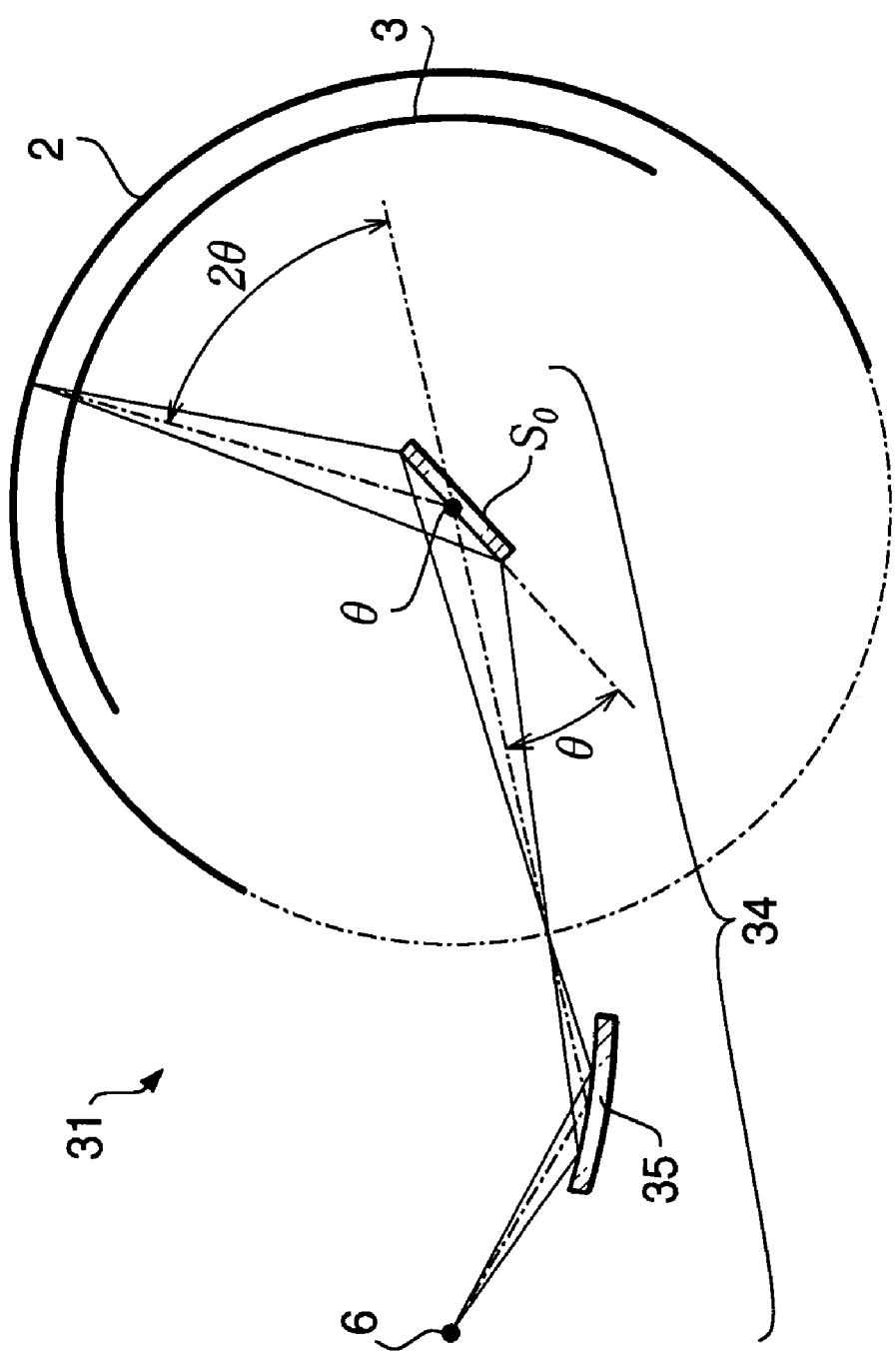
FIG. 3 is a schematic plan view of another embodiment of apparatus for X-ray analysis according to the present invention.

FIG. 3 illustrates another embodiment of apparatus for X-ray analysis according to the invention. FIG. 3 is a plan view of the embodiment of apparatus 31 for X-ray analysis. The apparatus 31 for X-ray analysis differs from the apparatus 1 for X-ray analysis shown in FIG. 1 in that, unlike the focusing optical system 4 of FIG. 1, a focusing optical system 34 of this embodiment comprises a curved crystal monochromater 35. The components of the focusing optical system 34 that are the same as those of the focusing optical system 4 are denoted respectively by the same reference symbols and will not be described any further.

A monochromater is arranged at the incident side relative to the specimen S0 in this embodiment. In other words, an incident monochromater is provided in this embodiment. Thus, it is possible to take out characteristic X-rays out of continuous X-rays generated by the X-ray source 6 and supply them to the specimen S0 so that unnecessary scattering X-rays can be removed to enhance the level of accuracy of measurement.

OTHER EMBODIMENTS

While the present invention is described above by way of preferred embodiments, the present invention is by no means limited to the above described embodiments, which may be modified and altered in various different ways without departing from the scope of the present invention as defined in the appended claims.

For instance, the means for supporting the mask 3 in FIG. 1 may have a structure other than that of the support frame 22. The common table 21 for supporting the diverging slit 11 in FIG. 1 and the collimator 16 in FIG. 2 may also have any appropriate structure.

What is claimed is:

1. An apparatus for X-ray analysis comprising:
 a focusing optical system formed by arranging an X-ray source adapted to generate X-rays, specimen supporting means for supporting a specimen and two-dimensional X-ray detecting means for detecting X-rays from the specimen so as to satisfy requirements of the focusing optical system;
 means for shifting an angle of incidence of X-rays relative to the specimen by rotating said specimen or said X-ray source around a central axis of rotation passing through a surface of the specimen;
 means for moving said two-dimensional X-ray detecting means in parallel with said central axis of rotation; and
 a mask arranged at a position in front of said two-dimensional X-ray detecting means as viewed from said specimen and having a slit on a line intersecting a plane rectangularly intersecting said central axis of rotation and containing a central optical axis of incident X-rays.

2. An apparatus according to claim 1, further comprising:
 X-ray beam switching means adapted to switch an X-ray beam striking the specimen from a divergent beam to a parallel beam or vice versa.

3. An apparatus according to claim 2, further comprising:
mask supporting means arranged so as to allow said mask to move between a first position located in front of said two-dimensional X-ray detecting means and a second position not located in front of said two-dimensional X-ray detecting means as viewed from said specimen.

4. An apparatus according to claim 1, wherein the shift of the angle of incidence of X-rays relative to the specimen and the parallel movement of said two-dimensional X-ray detecting means are synchronized with each other.

5. An apparatus according to claim 2, wherein the shift of the angle of incidence of X-rays relative to the specimen and the parallel movement of said two-dimensional X-ray detecting means are synchronized with each other.

6. An apparatus according to claim 3, wherein the shift of the angle of incidence of X-rays relative to the specimen and the parallel movement of said two-dimensional X-ray detecting means are synchronized with each other.

7. An apparatus according to claim 1, wherein
an X-ray receiving surface of said two-dimensional X-ray detecting means is that of a cylinder formed around the central axis of rotation.

8. An apparatus according to claim 2, wherein
an X-ray receiving surface of said two-dimensional X-ray detecting means is that of a cylinder formed around the central axis of rotation.

9. An apparatus according to claim 3, wherein
an X-ray receiving surface of said two-dimensional X-ray detecting means is that of a cylinder formed around the central axis of rotation.

10. An apparatus according to claim 4, wherein
an X-ray receiving surface of said two-dimensional X-ray detecting means is that of a cylinder formed around the central axis of rotation.

11. An apparatus according to claim 5, wherein
an X-ray receiving surface of said two-dimensional X-ray detecting means is that of a cylinder formed around the central axis of rotation.

12. An apparatus according to claim 6, wherein
an X-ray receiving surface of said two-dimensional X-ray detecting means is that of a cylinder formed around the central axis of rotation.

13. A method for X-ray analysis in which X-rays from an X-ray source to strike a specimen are switched between a divergent beam and a parallel beam, and X-rays which emerge from said specimen are detected by a two-dimensional X-ray detecting means, said method having a measuring step using said divergent beam, said measuring step using said divergent beam comprising the steps of:
shifting an angle of incidence of X-rays striking said specimen by rotating either said specimen or said X-ray source around a central axis of rotation running through a surface of the specimen;
arranging a mask having a slit in front of said two-dimensional X-ray detecting means so as to make the slit to be located on a line intersecting a plane rectangularly intersecting said central axis of rotation and containing a central optical axis of incident X-rays; and
moving said two-dimensional X-ray detecting means in parallel with said central axis of rotation in synchronism with the shift of the angle of incidence of X-rays relative to the specimen.

14. A method for X-ray analysis in which an X-ray striking a specimen is switched from a divergent beam formed by a diverging slit to a parallel beam formed by a collimator or vice versa, and X-rays which emerge from said specimen are detected by a same two-dimensional X-ray detecting means, wherein
a step of using said divergent beam comprises the steps of:
shifting an angle of incidence of X-rays striking said specimen by rotating either said specimen or an X-ray source around a central axis of rotation running through a surface of the specimen;
arranging a mask having a slit in front of said two-dimensional X-ray detecting means so as to make the slit to be located on a line intersecting a plane rectangularly intersecting said central axis of rotation and containing a central optical axis of incident X-rays; and
moving said two-dimensional X-ray detecting means in parallel with said central axis of rotation in synchronism with the shift of the angle of incidence of X-rays relative to the specimen.

* * * * *